(12) United States Patent
Ischdonat et al.

(10) Patent No.: US 7,384,510 B2
(45) Date of Patent: *Jun. 10, 2008

(54) APPARATUS AND METHOD FOR DETERMINING THE PERMEABILITY OF A CIRCULATING BAND IN A PAPER MACHINE

(75) Inventors: Thomas Ischdonat, Bachhagel (DE); Ralf Pfifferling, Gerstetten (DE); Rudolf Muench, Koenigsbronn (DE); Michael Sollinger, Stuttgart (DE); Wolfgang Ulfert, Tettnang (DE)

(73) Assignee: Voith Patent GmbH, Heidenheim (DE)

( * ) Notice: Subject to any disclaimer, the term of this patent is extended or adjusted under 35 U.S.C. 154(b) by 487 days.

This patent is subject to a terminal disclaimer.

(21) Appl. No.: 10/943,690

(22) Filed: Sep. 17, 2004

(65) Prior Publication Data

US 2005/0145358 A1 Jul. 7, 2005

(30) Foreign Application Priority Data

Sep. 19, 2003 (DE) .............................. 103 43 913

(51) Int. Cl.
*D21F 7/06* (2006.01)

(52) U.S. Cl. ...................... 162/263; 162/272; 162/198; 162/199; 73/38

(58) Field of Classification Search ................ 162/199, 162/272, 263, 198; 73/38

See application file for complete search history.

(56) References Cited

U.S. PATENT DOCUMENTS

| 4,880,499 A | 11/1989 | Pikulik .................... 162/263 |
| 5,725,737 A | 3/1998 | Pikulik et al. .............. 162/263 |
| 6,092,003 A | 7/2000 | Hagart-Alexander et al. .... 700/129 |
| 6,266,999 B1 | 7/2001 | Arnshav ....................... 73/38 |

FOREIGN PATENT DOCUMENTS

| EP | 0 024 205 | 8/1980 |
| EP | 0 383 486 A2 | 8/1990 |

*Primary Examiner*—Mark Halpern
(74) *Attorney, Agent, or Firm*—Taylor & Aust, P.C.

(57) ABSTRACT

An apparatus and a method for determining the permeability of a circulating band, in particular a water-absorbing dewatering band in a papermaking machine. The apparatus is equipped with a nozzle from which a measuring fluid flows onto or through the band. Fluctuations in the flow of the measuring fluid and in the nozzle exit pressure can distort the measurement of the permeability. The apparatus has a device for determining the speed of the band and/or a device for determining the nozzle exit speed and the nozzle exit pressure of the measuring fluid. These three measured variables are measured simultaneously, so that a fluctuation in one of these measured variables cannot impair the accuracy of the permeability measurement.

24 Claims, 2 Drawing Sheets

APPARATUS AND METHOD FOR DETERMINING THE PERMEABILITY OF A CIRCULATING BAND IN A PAPER MACHINE

BACKGROUND OF THE INVENTION

1. Field of the Invention

The present invention relates to an apparatus for determining the permeability of a circulating band, in particular a water-absorbing dewatering band in a papermaking machine, having a nozzle from which a measuring fluid flows onto or through the band.

2. Description of the Related Art

In general, apparatuses for measuring the permeability at circulating bands are known. In these apparatuses, water is pressed through the band and the permeability of the band is determined by way of a pressure measurement. However, the disadvantage with the apparatuses known is that these require either a constant water pressure or a constant water flow. If the water pressure or water flow cannot be kept constant, the measured result is distorted.

What is needed in the art is an improved apparatus which permits an accurate determination of the permeability even in the event of variable flow conditions in the measuring fluid.

SUMMARY OF THE INVENTION

The present invention provides as apparatus for determining the permeability of a circulating band which permits an accurate determination of the permeability even in the event of variable flow conditions in the measuring fluid.

The invention comprises, in one form thereof, an apparatus for determining the permeability of a circulation band which includes a device for determining the speed of the band and/or a device for determining the nozzle exit speed and nozzle exit pressure of the measuring fluid. As a result of the simultaneous measurement of the band speed, the nozzle exit speed and the nozzle exit pressure, the apparatus is independent of fluctuations in pressure or speed conditions of the measuring fluid during the determination of the permeability. Thus, the apparatus always supplies an accurate value for the permeability. In addition, the apparatus according to the present invention permits a high measuring speed and a high resolution of the measured points along the width of the band. For instance, it is possible to carry out a measurement every two millimeters. It is likewise advantageous that the measurements can be carried out while the circulating band is in operation. The apparatus according to the present invention makes it possible to follow the permeability over the entire duration of use of the band. As a result, an operator is able to estimate the remaining lifetime of the band and to plan a band change in good time. In this way, unforeseen downtimes can be ruled out. In this way, not only is it possible to characterize local faults quantitatively but the creation of a "permeability map" with good resolution is also possible. However, a precondition for this is the presence both of a band trigger and also of a displacement transducer on the traversing measuring head.

The device for determining the nozzle exit speed and the nozzle exit pressure can have an orifice plate, at which in each case a pressure sensor is arranged on both sides. By way of this arrangement, a pilot pressure prevailing upstream of the orifice plate in the flow direction can be kept constant, and a flow rate can be set by way of the pressure drop across the orifice plate. The nozzle exit pressure can be measured by the pressure sensor downstream of the orifice plate. The nozzle exit speed can be calculated through the pilot pressure upstream of the orifice plate and the nozzle exit pressure downstream of the orifice plate. The nozzle exit pressure advantageously lies between 10 and 50 bar, pressures between 15 and 30 bar supplying good results.

In order to be able to influence the nozzle exit pressure and the nozzle exit speed, the opening in the orifice plate can be variable.

Depending on the permeability of the band, the ratio between the nozzle opening and the orifice plate opening can lie in an interval from 0.25 to 4. A small nozzle opening ratio is suitable for highly permeable bands and a high nozzle opening ratio for less permeable bands.

The device for determining the speed of the band is particularly operationally safe and reliable if it is equipped with an optical sensor. The optical sensor detects a point on the band which circulates again and again and is advantageously a band seam, at which the two ends of the endlessly circulating band are joined.

In order that the measuring fluid, which is advantageously water, has the same temperature as the band in its operation, in a further embodiment the apparatus can be equipped with a temperature sensor for measuring the temperature of the band. Of course, the temperature measurement of the measuring fluid can also be carried out during operation. In a further embodiment, the temperature of the band and the moisture of the band can be measured simultaneously, preferably by way of one and the same traversing unit.

In order to be able to compensate for a temperature difference between the temperature of the measuring fluid and the temperature of the band, the temperature sensor can be connected to at least one heating device for heating up the measuring fluid. The temperature sensor then regulates the temperature of the measuring fluid to the temperature value of the band via the heating device. A measurement of the permeability is then ensured under the operating conditions of the band, such as those which prevail during the dewatering of a fibrous web.

In a development of the present invention, the device for determining the speed of the band and/or the device for determining the nozzle exit speed and the nozzle exit pressure and/or the temperature sensor are connected to a data processing unit. The data processing unit evaluates the measured values. The data processing unit can be connected to a cleaning assembly, which receives the evaluated measured results from the data processing unit. If there are critical measured values, the cleaning assembly is then able to clean the band at the relevant points.

In order to permit a compact and thus space-saving design, the nozzle and/or the temperature sensor can be arranged on a measuring head. In addition, the measuring head ensures that the nozzle is applied to the band at right angles.

In order to obtain accurate measured results, the measuring head can have a defined measuring area. For this reason, the measuring head can have a contact surface which can be pressed onto the band. However, it is also possible for the measuring head to be constructed as a frame which delimits the accurately defined measuring area.

If the frame is provided with sliding shoes and/or rollers, the circulating band can be moved continuously with relatively little friction under the frame pressed on.

In a development of the invention, the measuring head is produced from an abrasion-resistant material, in order that the service lives of the measuring head are as long as possible. Materials worth recommending for the measuring head are ceramic materials.

In order that an optimal measurement is ensured, the measuring head can be pressed against the band with a specific contact pressure and/or the nozzle within the measuring head can additionally be pressed against the band independently of the contact pressure of the measuring head. Since the accuracy of the measured result depends on the contact pressure of the nozzle against the band, the contact force for the contact pressure of the nozzle can be provided with a safety margin of 1 to 20. Good measured results can be achieved if the contact pressure of the measuring head against the band lies between 200 N/m² and 1500 N/m². Very good measured results are achieved in particular at 400 N/m² and 800 N/m².

In a development of the present invention, the apparatus has a compressor, in order to achieve a desired pressure for the measuring fluid. In a preferred embodiment, the compressor is an axial piston pump because of its beneficial operating behavior.

The apparatus can advantageously be provided with a device for damping pulsations since, because of the accuracy of the measured result, it is important to avoid pulsations with respect to the pressure and the flow velocity. It is very simple in constructional terms if the device for damping pulsations is a compressed air vessel.

In addition, the present invention relates to a method for measuring the permeability of a circulating band, in particular a water-absorbing dewatering band in a papermaking machine, having an apparatus as claimed in at least one of the claims, which comprises the following steps:
a) producing a measuring fluid volume flow,
b) applying the measuring fluid volume flow to the circulating band,
c) moving the measuring head to a first measuring point between the two band edges,
d) placing the measuring head on the band,
e) measuring the measuring fluid pressure upstream of the orifice plate, the measuring fluid pressure downstream of the orifice plate and the band speed,
f) repeating step e) for the remaining measuring points between the two band edges.

The measured permeability signal is in this case composed of a plurality of components. According to Bernoulli: $p+\frac{1}{2}p \cdot v^2$=constant. The measured signal can accordingly be understood as a sum of different dynamic pressures: permeability=f(p)=f(dv/dt (band permeability))+f(v(band))+f(nozzle geometry). The variable f(v(band)) is composed of the volume V1 of the band under the nozzle opening of the measuring device and the speed of the band: f(dv/dt(band))=V1·v(band). The variable f(nozzle geometry) depends substantially on the set pilot pressure, the contact pressure of the nozzle device on the band, the nozzle diameter and the nozzle geometry, f(nozzle geometry)<<f(v(band))||f(band permeability).

In the case of the method according to the present invention, the measured values can be evaluated in the data processing unit in a following step. In the next step, the cleaning assembly connected to the data processing unit is able to clean the band at relevant points following the measured value evaluation. The present invention likewise relates to a forming section of a papermaking machine which is equipped with an apparatus as claimed in at least one of the claims. The present invention likewise includes a press section of a papermaking machine which is equipped with an apparatus as claimed in at least one of the claims.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
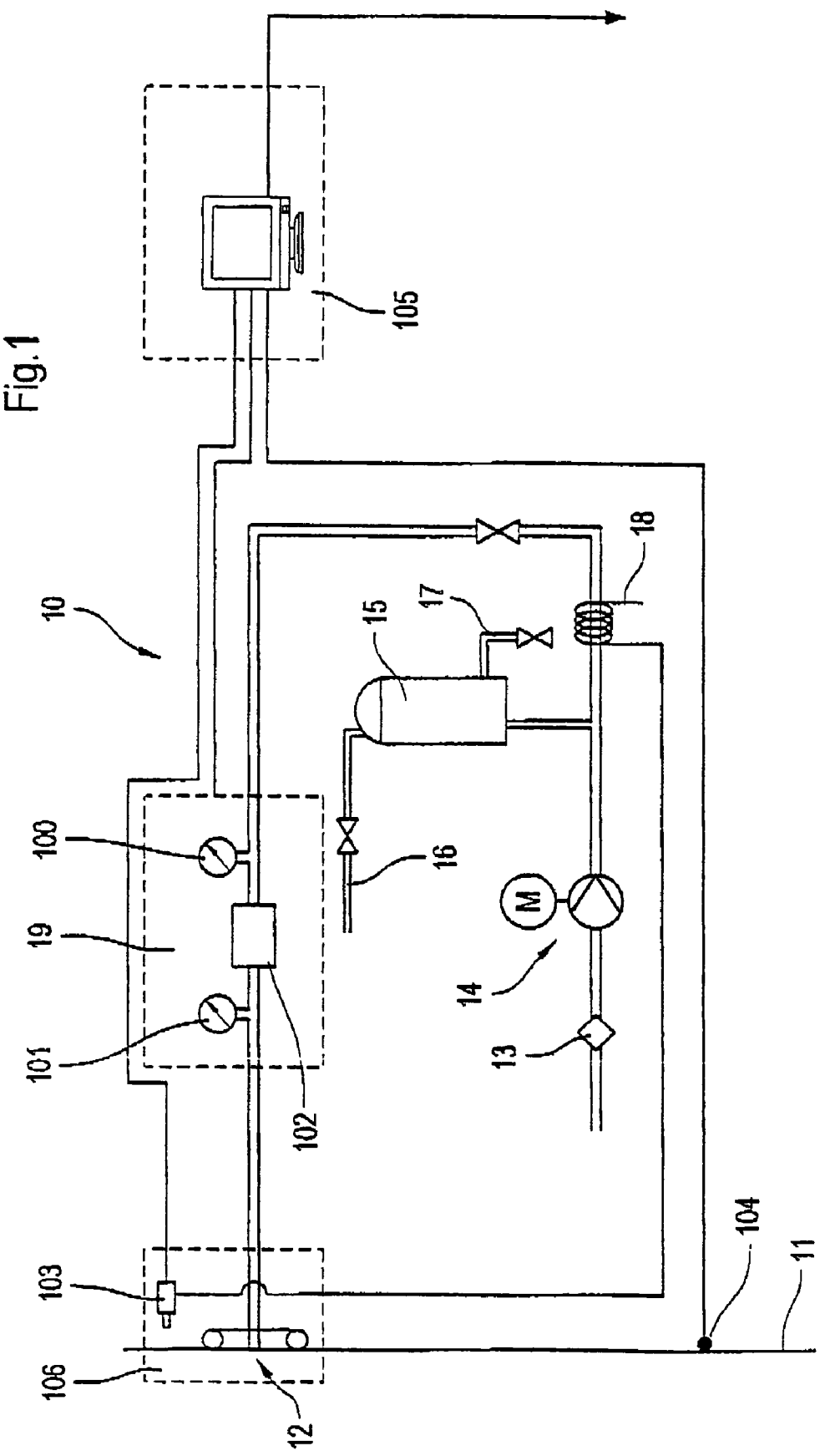
FIG. 1 is a schematic view of the apparatus according to the invention.

Referring now to the drawings, and more particularly to FIG. 1, there is shown a FIG. 1 shows an apparatus 10 for determining the permeability of a circulating band 11, which is a water-absorbing dewatering band in a papermaking machine. From a nozzle 12, a measuring fluid, which can preferably be water, flows onto band 11. The measuring fluid is cleaned in a filter 13 and is brought to a specific operating pressure by using a preferably pressure-regulated compressor 14. This operating pressure can lie between 10 and 50 bar, very good measured results being achieved in particular at 15 to 30 bar. Downstream of compressor 14, the measuring fluid is connected to a compressed air vessel 15, which is acted on with a specific air pressure in order to damp pulsations of the measuring fluid.

Before the measurement, pressure vessel 15 is emptied via pressure line 17 down to the level of the outlet. Pressure line 17 is then closed and ventilation line 16 is opened, compressed air vessel 15 is filled with compressed air, and ventilation line 16 is then closed. The enclosed compressed air serves as an air pad for damping pulsations. With the aid of compressor 14, the operating pressure of the measuring fluid is then regulated. The air pad is accordingly compressed. The measuring fluid does not flow through compressed air vessel 15. After passing the compressed air vessel 15, the measuring fluid is heated up to the operating temperature of band 11 by a heating device 18 preferably having a temperature sensor. From heating device 18, the measuring fluid passes to a device 19 which has pressure sensors 100 and 101 and an orifice plate 102. By way of device 19, it is thus possible, by way of the pressures measured upstream and downstream of orifice plate 102 in the flow direction, for the exit speed of the measuring fluid from nozzle 12 and its exit pressure from nozzle 12 to be determined. A temperature sensor 103 measures the temperature of band 11. It is connected to heating device 18, so that the temperature of the measuring fluid can always be regulated to the operating temperature of band 11. Apparatus 10 is also provided with a device 104 for measuring the band speed. Device 104 can be an optical sensor which detects a periodically circulating marking and thus determines the band speed. Device 19, temperature sensor 103 and device 104 are each connected to a data processing unit 105. With the aid of the pressures measured by device 19 and device 104, the nozzle exit speed and the band speed, data processing unit 105 can determine the permeability. Data processing unit 105 evaluates the measured values and passes then on to a cleaning assembly, not specifically illustrated here. The cleaning assembly is able to clean the relevant points on band 11 as required. Nozzle 12 and temperature sensor 103 are combined in a measuring head 106. Nozzle 12 is arranged at right angles to band 11 in the measuring head 106, in order that measuring fluid can be forced through band 11 in an optimum manner. Measuring head 106, together with nozzle 12, is pressed against band 11 with a specific contact pressure. Both the measuring head 106 and the nozzle 12 can be pressed against the band 11 with a specific contact pressure, respectively independently of each other.

Figure 2:
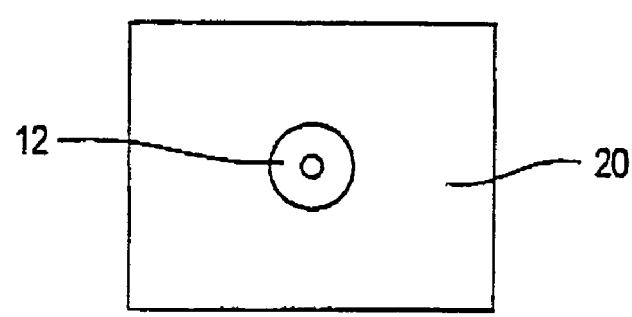
FIG. 2 is a plan view of a first embodiment of a measuring head.
Figure 3:
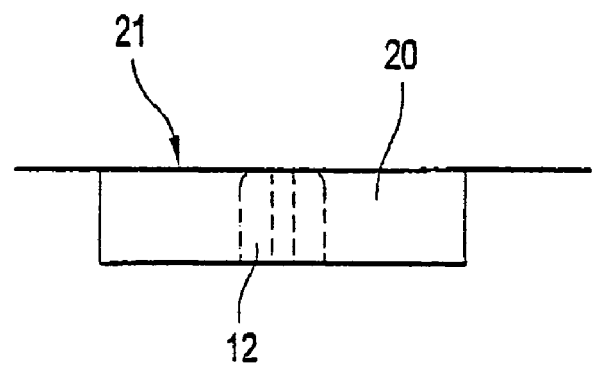
FIG. 3 is a side view of the measuring head from FIG. 2.

FIGS. 2 and 3 show a measuring head 20 which has a contact surface 21 which can be pressed on in order to press measuring head 20 against band 11. The contact surface 21 represents a defined measuring area for the measurement to be carried out. Nozzle 12 is likewise arranged in measuring head 20.

Figure 4:
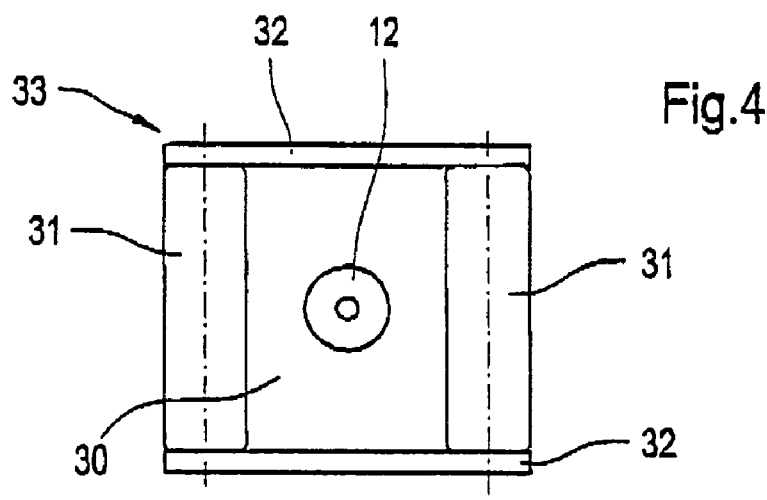
FIG. 4 is a plan view of a second embodiment of a measuring head.
Figure 5:
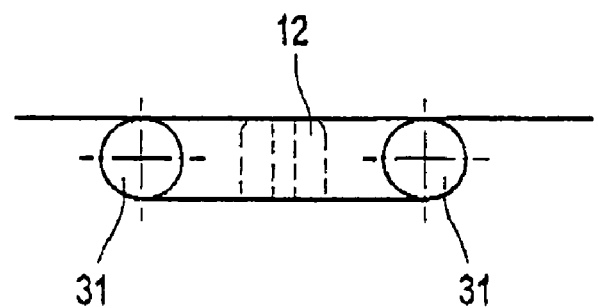
FIG. 5 is a side view of the measuring head from FIG. 4.

FIGS. 4 and 5 show measuring head 30 as a further embodiment. Measuring head 30 is provided with rollers 31, with which it is pressed against band 11. When measuring head 30 is pressed on, band 11 can thus be led through under rollers 31 with relatively little friction. Rollers 31 are mounted in connecting elements 32 so that, together with rollers 31, they form a frame 33. Nozzle 12 is arranged in frame 33. Frame 33 defines the measuring area for the measurement to be carried out.

Measuring heads 20 and 30 ensure a defined measuring area, with which band 11 is in contact during the permeability measurement. Furthermore, nozzle 12 is arranged in measuring heads 20 and 30 at right angles to the course of band 11, which ensures that the measuring fluid strikes band 11 at right angles and thus ensures an optimal permeability measurement.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF DESIGNATIONS

10 Apparatus
11 Band
12 Nozzle
13 Filter
14 Compressor
15 Compressed air vessel
16 Ventilation line
17 Pressure line
18 Heating device
19 Device
20 Measuring head
21 Contact surface
30 Measuring head
31 Roller
32 Connecting element
33 Frame
100, 101 Pressure sensor
102 Orifice plate
103 Temperature sensor
104 Device
105 Data processing unit
106 Measuring head

What is claimed is:

1. An apparatus for determining a permeability of a circulating band in a papermaking machine, comprising:
   a nozzle from which a measuring fluid flows at least one of onto the circulating band and through the circulating band, said measuring fluid including both a nozzle exit speed and a nozzle exit pressure;
   a device for determining said nozzle exit speed and said nozzle exit pressure; and
   a device for determining a speed of the circulating band.

2. The apparatus of claim 1, wherein said circulating band is a water-absorbing dewatering band.

3. The apparatus of claim 1, wherein said device for determining said nozzle exit speed and said nozzle exit pressure includes an orifice plate with a first side and a second side, each of said first side and said second side includes at least one pressure sensor.

4. The apparatus of claim 3, wherein said orifice plate includes an orifice plate opening which is variable.

5. The apparatus of claim 4, wherein said nozzle includes a nozzle opening, a ratio between said nozzle opening and said orifice plate opening is approximately between 0.25 to 4.

6. The apparatus of claim 1, wherein said device for determining said speed of the circulating band is equipped with an optical sensor.

7. The apparatus of claim 1, further including a temperature sensor for measuring a temperature of the circulating band.

8. The apparatus of claim 7, further including at least one heating device for heating said measuring fluid, said temperature sensor being connected to said at least one heating device.

9. The apparatus of claim 7, further including a data processing unit connected to at least one of said device for determining said speed of the circulating band, said device for determining said nozzle exit speed and said nozzle exit pressure and said temperature sensor.

10. The apparatus of claim 9, further including a cleaning assembly connected to said data processing unit.

11. The apparatus of claim 7, further including a measuring head, at least one of said nozzle and said temperature sensor being arranged on said measuring head.

12. The apparatus of claim 11, wherein said measuring head has a contact surface which is pressed onto the circulating band.

13. The apparatus of claim 11, wherein said measuring head is constructed as a frame.

14. The apparatus of claim 13, wherein said frame is provided with at least one of a plurality of sliding shoes and a plurality of rollers.

15. The apparatus of claim 11, wherein said measuring head is produced from an abrasion-resistant material.

16. The apparatus of claim 11, wherein at least one of said measuring head is pressed against the circulating band with a specific contact pressure and said nozzle being within said measuring head is pressed against the circulating band independently of said specific contact pressure of said measuring head.

17. The apparatus of claim 16, further including a contact pressure associated with said nozzle, said contact pressure having an associated contact force including a safety margin of approximately between 1 and 20.

18. The apparatus of claim 16, wherein said specific contact pressure is approximately between 200 N/m$^2$ and 1500 N/m$^2$.

19. The apparatus of claim 1, further including a compressor connected to said nozzle.

20. The apparatus of claim 19, wherein said compressor is an axial piston pump.

21. The apparatus of claim 1, further including a device for damping pulsations connected to said nozzle.

22. The apparatus of claim 21, wherein said device for damping pulsations is a compressed air vessel.

23. A forming section of a papermaking machine, comprising:

a nozzle from which a measuring fluid flows at least one of onto a circulating band and through the circulating band, said measuring fluid including both a nozzle exit speed and a nozzle exit pressure;

a device for determining said nozzle exit speed and said nozzle exit pressure; and a device for determining a speed of the circulating band.

24. A press section of a papermaking machine, comprising:

a nozzle from which a measuring fluid flows at least one of onto a circulating band and through the circulating band, said measuring fluid including both a nozzle exit speed and a nozzle exit pressure;

a device for determining said nozzle exit speed and said nozzle exit pressure; and a device for determining a speed of the circulating band.

* * * * *